United States Patent
Wilcko (10) Patent No.: US 6,589,052 B1
(45) Date of Patent: Jul. 8, 2003

(54) ENDODONTIC INSTRUMENTS

(76) Inventor: James M. Wilcko, 1351 Timber Ridge Dr., Erie, PA (US) 16509

( * ) Notice: Subject to any disclaimer, the term of this patent is extended or adjusted under 35 U.S.C. 154(b) by 0 days.

(21) Appl. No.: 09/480,604

(22) Filed: Jan. 10, 2000

(51) Int. Cl.[7] ................................................ A61C 5/02
(52) U.S. Cl. ........................................................ 433/102
(58) Field of Search ................................ 433/102, 165, 433/224

(56) References Cited

U.S. PATENT DOCUMENTS

| | | | | |
|---|---|---|---|---|
| 1,063,109 A | * | 5/1913 | Bolls | 433/102 |
| 3,906,636 A | * | 9/1975 | Rainer et al. | 433/102 |
| 4,190,958 A | * | 3/1980 | Martin et al. | 433/102 |
| 4,299,571 A | | 11/1981 | McSpadden | |
| 4,332,561 A | | 6/1982 | McSpadden | |
| 4,443,193 A | | 4/1984 | Roane | |
| 4,536,159 A | | 8/1985 | Roane | |
| 4,611,508 A | | 9/1986 | Roane | |
| 4,661,061 A | * | 4/1987 | Martin | 433/102 |
| 4,850,867 A | | 7/1989 | Senia | |
| 4,934,934 A | | 6/1990 | Arpaio, Jr. | |
| 5,106,298 A | | 4/1992 | Heath | |
| 5,257,934 A | * | 11/1993 | Cossellu | 433/102 |
| 5,464,362 A | | 11/1995 | Heath | |
| 5,762,541 A | | 6/1998 | Heath | |
| 5,897,316 A | * | 4/1999 | Buchanan | 433/102 |

* cited by examiner

*Primary Examiner*—Ralph A. Lewis
(74) *Attorney, Agent, or Firm*—Fay, Sharpe, Fagan, Minnich & Mckee (57) ABSTRACT

A set of endodontic instruments for use in performing root canal therapy on a tooth each comprise a shaft, a cutting head on the shaft having a frusto-conical cutting surface tapering inwardly of a shaft from a base end to a second end of the cutting head, and a follower extending from the second end of the cutting head to the distal end of the instrument. The cutting surfaces of a set of the endodontic instruments have different lengths and different tapers between the base and second ends thereof. A pair of retaining spring wires are helically wound in opposite directions about the shaft and are connected to the shaft and to the cutting head to preclude total separation of the cutting head and shaft in the event of breakage of the shaft.

49 Claims, 4 Drawing Sheets

ENDODONTIC INSTRUMENTS

BACKGROUND OF THE INVENTION

The present invention relates to the art of endodontic instruments such as files and reamers for use in performing root canal therapy on a tooth and, more particularly, to improved instruments for the latter purpose.

It is of course well known that the field of endodontics relates to the cleaning and enlargement of the root canals of human teeth for the purpose of removing organic materials and extraneous material present in the root canal and for enlarging the canal so that it can be filled. The diameter of the canals inside the root or roots of a tooth is very small, ranging from about 0.06 mm to about 0.2 mm at the apical tip. In order to perform the necessary therapy on the tooth, the upper end of the tooth is opened to access the hollow portion of the tooth, and a series or set of root canal files and/or reamers are utilized to remove the infected tissue within the canals and to enlarge the canals whereby the latter become mechanically sterilized and rendered large enough to receive the root canal filling material.

Two basic varieties of such endodontic instruments have been available heretofore for such root canal therapy, one of which is a tapered wire, usually of stainless steel or a nickel-titanium alloy, which is ground flat on three or four sides to provide a triangular or square cross-section, and which is then twisted to create a three-dimensional file with sharp edges and flutes between the edges. Examples of such endodontic files are shown for example in patents U.S. Pat. No. 4,443,193 to Roane, U.S. Pat. No. 4,536,159 to Roane, and U.S. Pat. No. 4,611,508 to Roane, which patents are hereby incorporated herein by reference for background purposes. The second variety of such endodontic instruments is formed using the same tapered wire of stainless steel or a nickel-titanium alloy, but the wire is hollow ground to provide cutting edges thereabout as opposed to being ground flat and twisted to provide the cutting edges. Examples of endodontic instruments in the latter category are shown, for example, in patents U.S. Pat. No. 4,299,571 to McSpadden, U.S. Pat. No. 4,332,561 to McSpadden, U.S. Pat. No. 4,934,934 to Arpaio, et al., U.S. Pat. No. 5,464,362 to Heath, et al., and U.S. Pat. No. 5,762,541 to Heath, et al., which patents are hereby incorporated herein by reference for background information. These instruments can be hand-operated for cutting in a tooth canal during the down or up stroke of the instrument in the canal, or they can be rotated such as through the use of powered drilling instruments.

Such endodontic files and reamers heretofore available are used in sets in which the tools increase in diameter from one to the next in the set. Among the disadvantages of such instruments is the fact that the sets are produced by different manufacturers and, accordingly, come in different sizes, shapes and the like. Moreover, too many individual or different instruments are required in order to achieve a desired canal therapy. For example, there are three standard lengths for the files, namely 21, 25 and 31 mm, and at least 26 widths or diameters are available from 0.06 mm to 1.4 mm. Furthermore, in order to assure having the ability to achieve a desired canal therapy in view of the differences in patient's teeth, a dentist may use several different brands of such instruments, whereby the cost of obtaining and maintaining a sufficient supply is undesirably high. This will be appreciated when it is realized that the cost of such instruments is in the range of $1.25 each to over $6.50 each, and the fact that it is not unusual to utilize 10 to 20 instruments for a root canal procedure. Still further, some of the instruments can only be used once, and when the flutes between cutting edges of an instrument are filled with debris, the cutting efficiency is drastically reduced. Still further, since many files or reamers in a series are necessary to gradually enlarge the root canal to the desired width, the root canal process is very inefficient and slow. A further disadvantage lies in the fact that root canals are often curved and the files and reamers lack sufficient flexibility to follow the path of the canal and often gauge the tooth laterally outwardly of the canal. The files and reamers are also prone to breakage and separation which leaves a portion of the instrument in the canal, and the removal of such a broken piece of the instrument is very difficult if not impossible and, in any event, very time consuming.

SUMMARY OF THE INVENTION

In accordance with the present invention, an improved endodontic instrument for performing root canal therapy is provided and by which the foregoing and other disadvantages of such instruments heretofore available are minimized or overcome. More particularly in this respect, an endodontic instrument in accordance with the invention includes a cutting head having a frusto-conical cutting surface tapering inwardly from a base end to a second end. Preferably, the base ends of successive instruments in a set are of the same diameter while the cutting surfaces have different lengths and different tapers between the base and second end. A follower extends from the second end to the distal end of the instrument to promote the instrument following a curved root canal, and in the last instrument in a set the follower is defined by the apex of the conical cutting surface. Preferably, the cutting surface includes an abrasive such as diamond dust, and the cutting head is integral with or attached to a shaft and is tethered to the shaft by a retaining arrangement which assures that the shaft and cutting head remain interconnected in the event of breakage of the shaft during a root canal procedure, whereby removal of the portion of the instrument in the canal is facilitated. The retaining arrangement advantageously enables the use of a small diameter shaft which increases the flexibility of the instrument and improves the ability of the instrument to follow a curved root canal. Moreover, the retaining arrangement is totally flexible and, preferably, is provided by one or more spring wires helically wound about the shaft and having opposite ends attached one to the cutting head and the other to the shaft. The frusto-conical cutting surface advantageously avoids flutes which can clog with debris and, preferably, opposite sides of the base end of the cutting head are truncated to provide passageways allowing the debris to move outwardly of the canal relative to the instrument. A further advantage is that considerably fewer instruments will be required to perform a given root canal therapy resulting in a considerable savings in the cost of having an undesirably large inventory of such endodontic instruments.

It is accordingly an outstanding object of the present invention to provide an improved endodontic instrument for use in performing root canal therapy on a tooth.

Another object is the provision of an instrument of the foregoing character having a structure which promotes obtaining the desired root canal therapy with fewer instruments than heretofore required.

A further object is the provision of an instrument of the foregoing character having a cutting head and a supporting shaft therefor and wherein an arrangement is provided for precluding complete separation of the cutting head and shaft in the event of breakage during a root canal procedure.

Still another object is the provision of an instrument of the foregoing character in which the cutting head is free of flutes, crevices or the like which can fill with debris during a root canal procedure, thus promoting longer cutting efficiency for the instrument.

Still another object is the provision of an instrument of the foregoing character which enables root canal therapy using fewer instruments than heretofore required and wherein each instrument is highly efficient in connection with the cutting action performed thereby, and wherein retention of a broken portion of an instrument is assured to facilitate removal of the portion of the instrument from a root canal in the event of breakage of the instrument.

Still another object is the provision of an instrument of the foregoing character having a flexibility and structural profile which promotes the instrument following a curved tooth root canal.

Still a further object is the provision of an instrument of the foregoing character wherein the base of the cutting head is of the same diameter for all of the instruments in a set and wherein the length and taper of the cutting surface progressively increases to a final configuration in which the distal end or follower portion of the instrument is defined by the apex of the conical cutting surface.

BRIEF DESCRIPTION OF THE DRAWINGS

The foregoing objects, and others, will in part be obvious and in part pointed out more fully hereinafter in conjunction with the written description of preferred embodiments of the invention illustrated in the accompanying drawings in which.

DESCRIPTION OF PREFERRED EMBODIMENTS

Figures 1, 2, 3, 4:
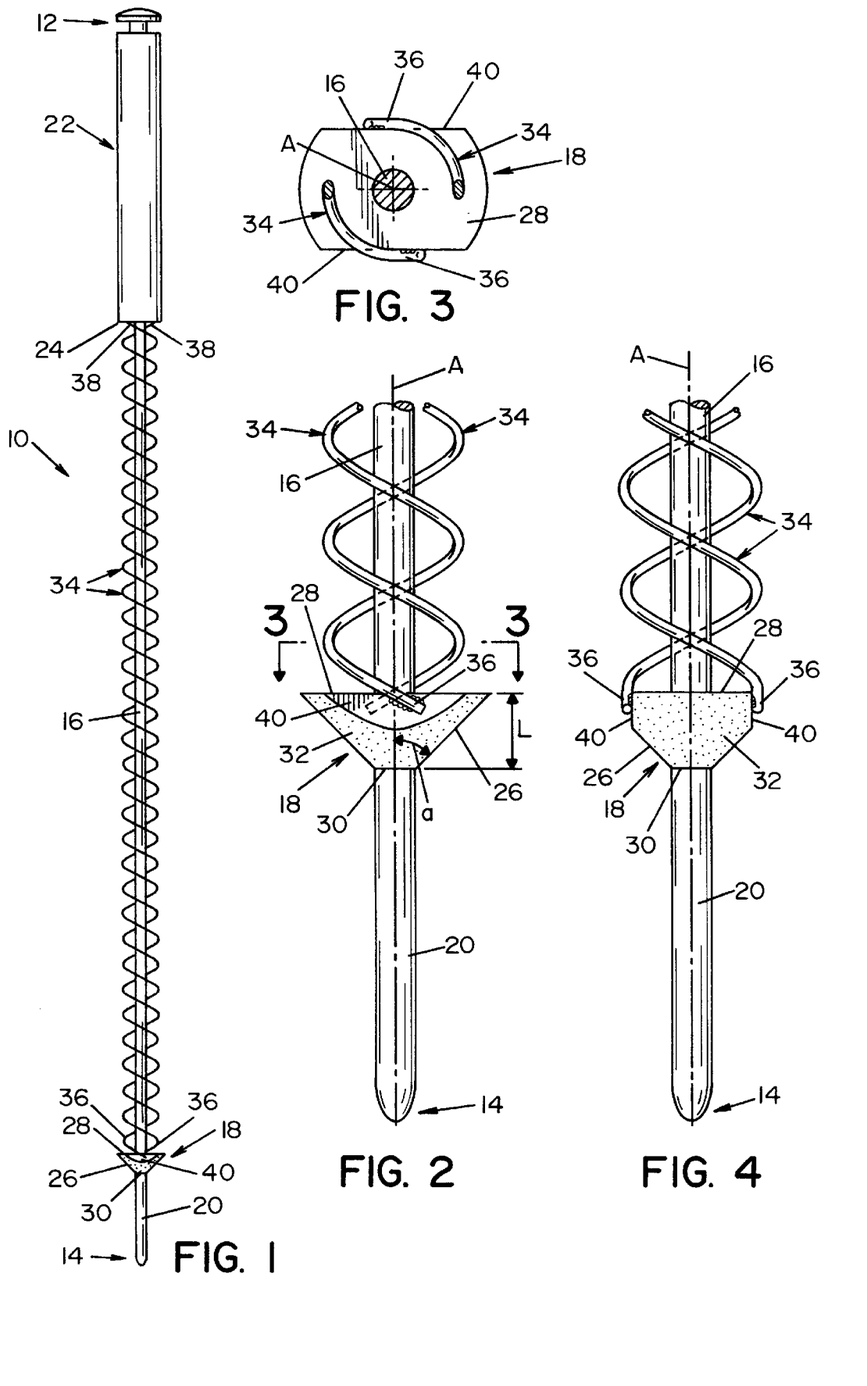
FIG. 1 is an elevation view of an endodontic instrument in accordance with the invention.
FIG. 2 is an enlarged elevation view of the cutting head and follower portion of the instrument shown in FIG. 1.
FIG. 3 is a cross-sectional view taken along line 3—3 in FIG. 2.
FIG. 4 is an side elevation view of FIG. 2 and looking in the direction from left to right in FIG. 2.

Referring now in greater detail to the drawings, wherein the showings are for the purpose of illustrating preferred embodiments of the invention only and not for the purpose of limiting the invention, FIG. 1 illustrates an endodontic instrument 10 which is the first of a set of instruments according to the invention and each of which instruments, as will become apparent hereinafter, includes a proximal end 12, a distal end 14, a shaft 16 extending from the proximal end toward the distal end, a cutting head 18 at a location spaced from the proximal end toward the distal end, and a follower 20 extending from the cutting head and providing distal end 14 of the instrument. Proximal end 12 can be defined by an attachment 22 on shaft 16 to mate with the chuck of a motorized dental hand-piece or drill or, alternatively, to provide a handle for manual manipulation of the instrument. The attachment has an end 24 spaced from proximal end 12 toward distal end 14, and the instrument has a length of 21, 25 or 31 mm from end 24 to distal end 14 thereof. As best seen in FIGS. 2 and 4, cutting head 18 includes a frusto-conical cutting surface 26 having a base end 28 and a second end 30 spaced from the base end in the direction toward distal end 14 of the instrument, and follower 20 extends from end 30 to distal end 14. Distal end of the instrument is the terminal end of follower 20 which, for the purpose set forth hereinafter, is rounded or of ellipsoidal profile and has a location axially on the latter profile which is tangential with a line between the location and the outer circular periphery of base end 28 of the cutting head. The cutting head has an axial length L between base end 28 and second end 30, and frusto-conical cutting surface 26 tapers inwardly from base end 28 toward second end 30 and has an angle of taper a with respect to axis A. Cutting surface 26 is provided with an abrasive material 32 which, preferably, is diamond dust. Referring again to FIG. 1, shaft 16 and follower 20 each have a diameter of about 0.25 mm, base end 28 of the cutting head has a diameter of about 1.1 mm, and the cutting head and follower have a length of from about 2.5 to 3.0 mm from base end 28 to distal end 14 of the instrument. The diameter for the base end of the cutting head is preferably the same for all of the instruments while the length L and angle of taper a of the cutting head vary between successive instruments in a set as will become apparent hereinafter. The shaft, cutting head and follower can be of one-piece construction shaped on a lathe, for example, and preferably from stainless steel or a titanium-nickel alloy. Alternatively, the head and follower can be of one piece construction and attached to the shaft such as by welding.

In accordance with one aspect of the invention, as best seen in FIG. 1, each of the endodontic instruments includes at least one and preferably two or more retaining members 34 having opposite ends 36 and 38 respectively connected to cutting head 18 and to shaft 16 at a location therealong spaced from head 18 toward proximal end 12 of the instrument. Retaining members 34 are preferably of spring wire helically wound in opposite directions about shaft 16 so as to be spaced radially outwardly therefrom, and ends 36 and 38 are suitably connected to the cutting head and shaft, such as by laser welds. Should shaft 16 break during a root canal procedure, which breakage most often occurs at the juncture between stem 16 and base end 28 of the cutting head, retaining members 34 preclude the parts of the instrument from becoming completely separated from one another, whereby removal of the portion in the root canal of a tooth is facilitated by twisting and/or pulling on the retaining members.

Preferably, at least one passageway is provided axially across cutting head 18 between cutting surface 26 and base end 28 to allow the tissue in a root canal to pass outwardly thereof past the cutting head during a root canal procedure. In the preferred embodiment, as best seen in FIGS. 2–4, two such passageways are provided by truncating diametrically opposite sides of base end 28 of the cutting head to provide planar surfaces 40 which interrupt the circular profile of base end 28 and provide passageways therealong. Further in connection with the preferred embodiment, ends 36 of retaining members 34 are welded or otherwise secured to planar surfaces 40 which afford an optimum area along the terminal portions of ends 36 for weldment thereto.

Figure 5:
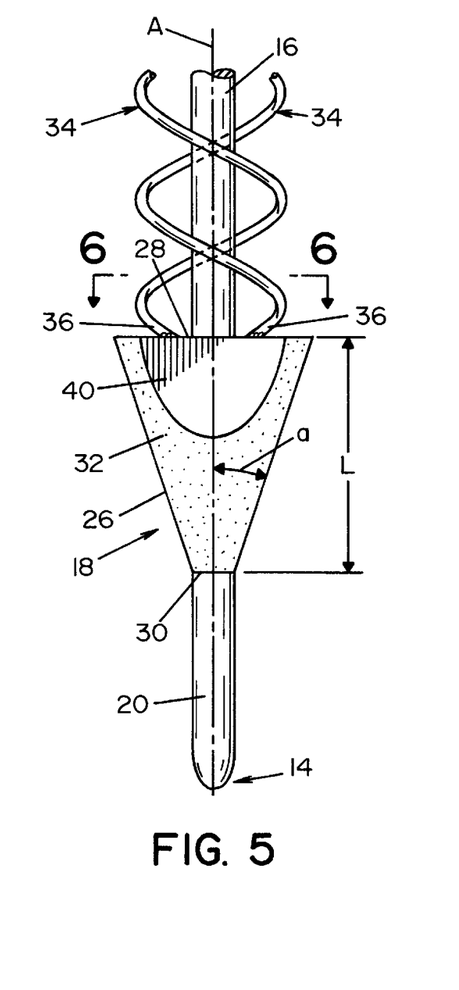
FIG. 5 is an enlarged elevation view of a second endodontic instrument in a set of instruments in accordance with the invention and showing a modification of the attachment of the retaining springs to the cutting head.
Figure 6:
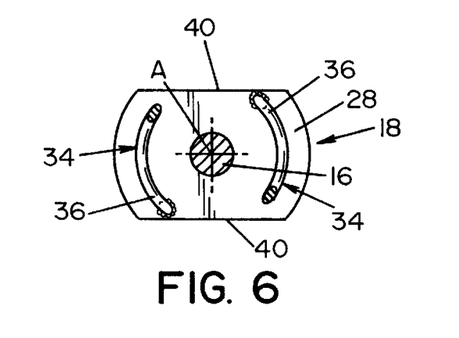
FIG. 6 is a cross-sectional view taken along line 6—6 in FIG. 5.

FIGS. 5 and 6 of the drawing illustrate a second endodontic instrument of a set of such instruments according to the invention. In this instrument, cutting head 18 has a length L and cutting head 18 has a length L and cutting surface 26 tapers at an angle a relative to axis A, and the length and angle of taper are respectively greater than and less than the length and angle of taper of the cutting surface of cutting head 18 of the first instrument of the set shown in FIGS. 1–4 of the drawing. Otherwise, the diameter of base end 28 and the length of the instrument from base end 28 to distal end 14 is the same as that described hereinabove in connection with the instrument shown in FIG. 1, and planar faces 40 are spaced the same distance from axis A as in the instrument shown in FIGS. 1–4. FIGS. 5 and 6 also illustrate a modification of the attachment of ends 36 of retaining members 34 to the cutting head, and in this respect ends 36 are welded or otherwise secured to base end 28 rather than planar surfaces 40. It will be appreciated that this modification of the attachment of ends 36 to the cutting head is applicable to the instrument shown in FIGS. 1–4.

Figure 7:
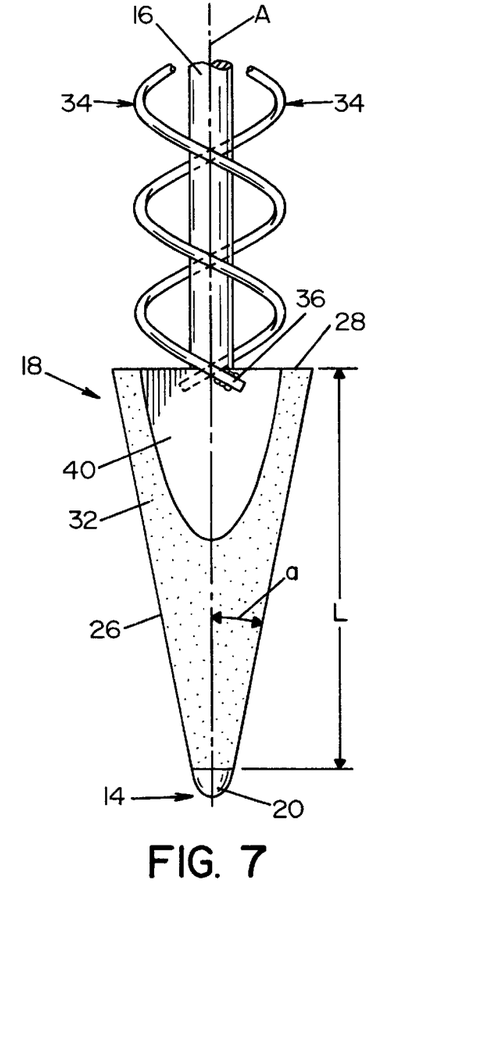
FIG. 7 is an enlarged elevation view of yet another endodontic instrument in a set of instruments according to the invention.

FIG. 7 illustrates a third endodontic instrument in a set of such instruments according to the invention. In this instrument, cutting head 18 has a length L and cutting surface 26 has an angle of taper a relative to axis A of the instrument, and the length and angle of taper are respectively greater than and less than the length and angle of taper of the instruments shown in FIGS. 2 and 5. Again, as in the instruments shown in FIGS. 1–6, the diameter of the base, the length of the instrument and the spacing of planar faces 40 from axis A is the same. Further, as will be appreciated from FIG. 7, distal end 14 of the instrument provides the follower portion thereof and, as described hereinabove, is ellipsoidal in profile providing for cutting surface 26 to be tangential with respect thereto and with respect to the circular periphery of the base end of the cutting surface.

It will be appreciated, of course, that a set of endodontic instruments in accordance with the invention can include any desired number of instruments in which succeeding and/or preceding instruments of the set have a cutting head including a frusto-conical cutting surface having a base end of constant diameter and having a length L and an angle of taper a which differs from one instrument to the next. This is shown, for example, in FIGS. 8 and 9 with respect to a set of six instruments in which the frusto-conical outer surface of successive instruments from that shown in FIG. 2 to that shown in FIG. 7 are designated 26a–26f, respectively, and in which the corresponding planar surfaces are designated 40a–40f, respectively. As will be further appreciated from FIGS. 8 and 9, each of the cutting surfaces 26a–26f has a corresponding angle of taper which progressively decreases in the direction from base end 28 of the cutting surface toward distal end 14 of the instrument, and a corresponding length which progressively increases from base end 28 of the cutting surface toward distal end 14 of the instrument. Again, it will be appreciated that any desired number of instruments can be provided in a given set depending on the desired incremental difference in the length L and angle of taper from one instrument to the next in the set.

Figures 8, 9, 10:
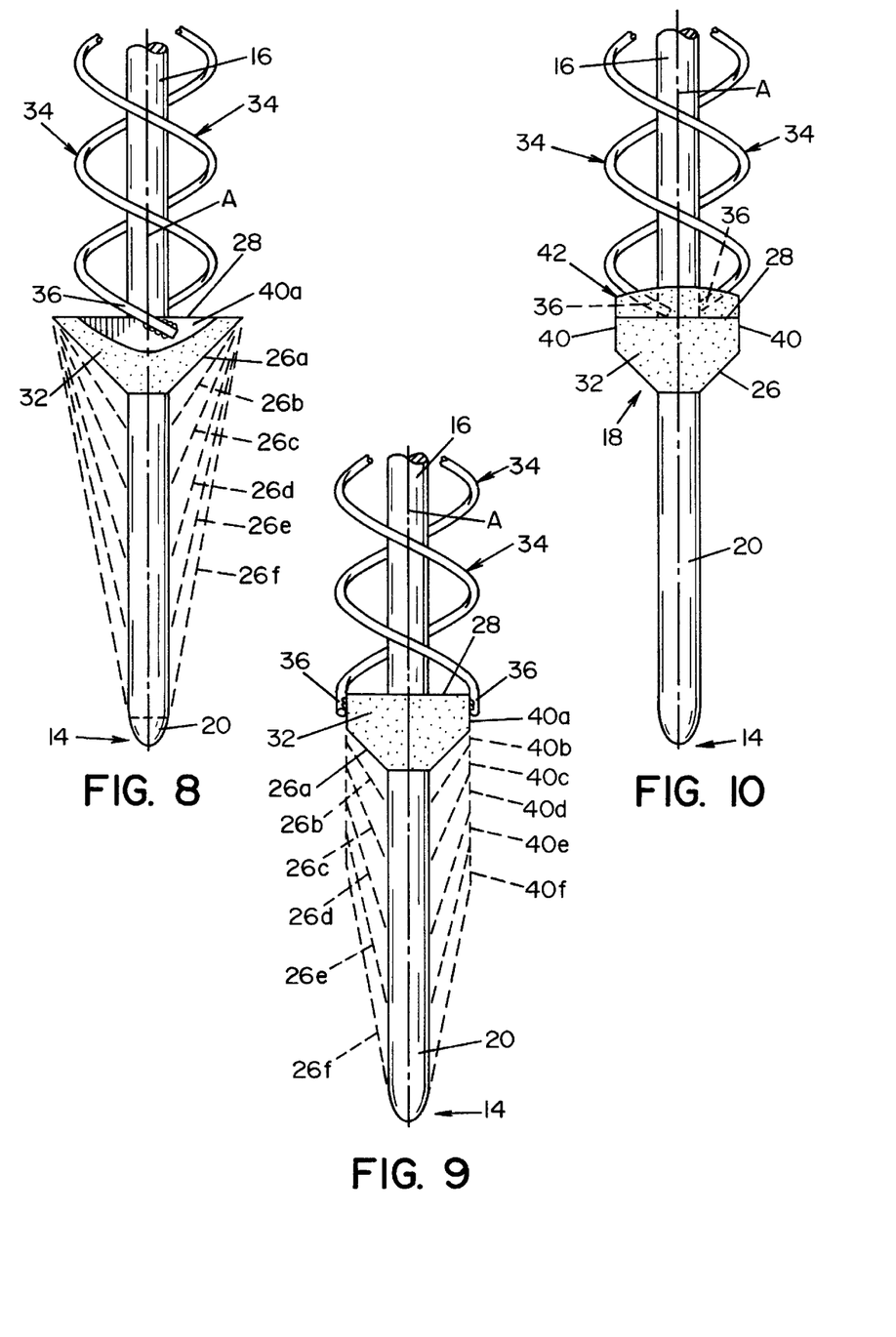
FIG. 8 is an enlarged elevation view similar to FIG. 2 and schematically illustrating a plurality of profiles for the cutting head between the profiles shown in FIGS. 1 and 7.
FIG. 9 is an enlarged elevation view similar to FIG. 4 and schematically illustrating the truncated end faces for the profiles shown in FIG. 8.
FIG. 10 is an enlarged elevation view illustrating a modification of the base portion of the cutting head of an endodontic instrument according to the invention; and, FIGS. 11A–11C somewhat schematically illustrate the stages of a root canal therapy using a set of endodontic instruments according to the invention.

FIG. 10 illustrates an arrangement for reinforcing the outer peripheral edge portion of the cutting head and the juncture between base end 28 and shaft 16. In this respect, cutting head 18 is provided with a reinforcement 42 which is separate from the cutting head and suitably secured to the base end 28 thereof in surrounding relationship with the corresponding portion of shaft 16 at the juncture thereof with the cutting head. The material of the reinforcement can be any material having sufficient strength to reinforce the outer peripheral edge portion of the cutting head against damage. More particularly in this respect, and with reference in particular to the instrument shown in FIG. 1, Reinforcing portion 42 advantageously axially reinforces the outer peripheral portion of cutting surface 26 at base end 28 of the cutting head against deterioration which would result from rotational and/or axial displacement of the instrument relative to a tooth canal in that the peripheral edge portion is relatively thin as a result of the angle of taper a for this instrument. While shown in connection with the instrument illustrated in FIGS. 1–4, it will be appreciated that a reinforcing portion of the cutting head can be used to advantage with others of the instruments in a set, especially those having the larger angles of taper and thus the lesser resistance to damage at the outer peripheral edge of the cutting surface. If the reinforcement is of metal, it can be applied to the base end of the cutting head such as by spatter deposition. Further, while shown and described as being separate from cutting head 18, it will be appreciated that the dome-shaped reinforcing portion could be machined integral with the shaft, cutting head and follower as in the previous embodiments. Ends 36 of reinforcing members 34 can be imbedded in the material of the reinforcing portion, secured to the outer surface thereof such as by laser welding if the reinforcing material is metal, or secured to planar surfaces 40 as in the previous embodiments.

Figures 11A, 11B, 11C:
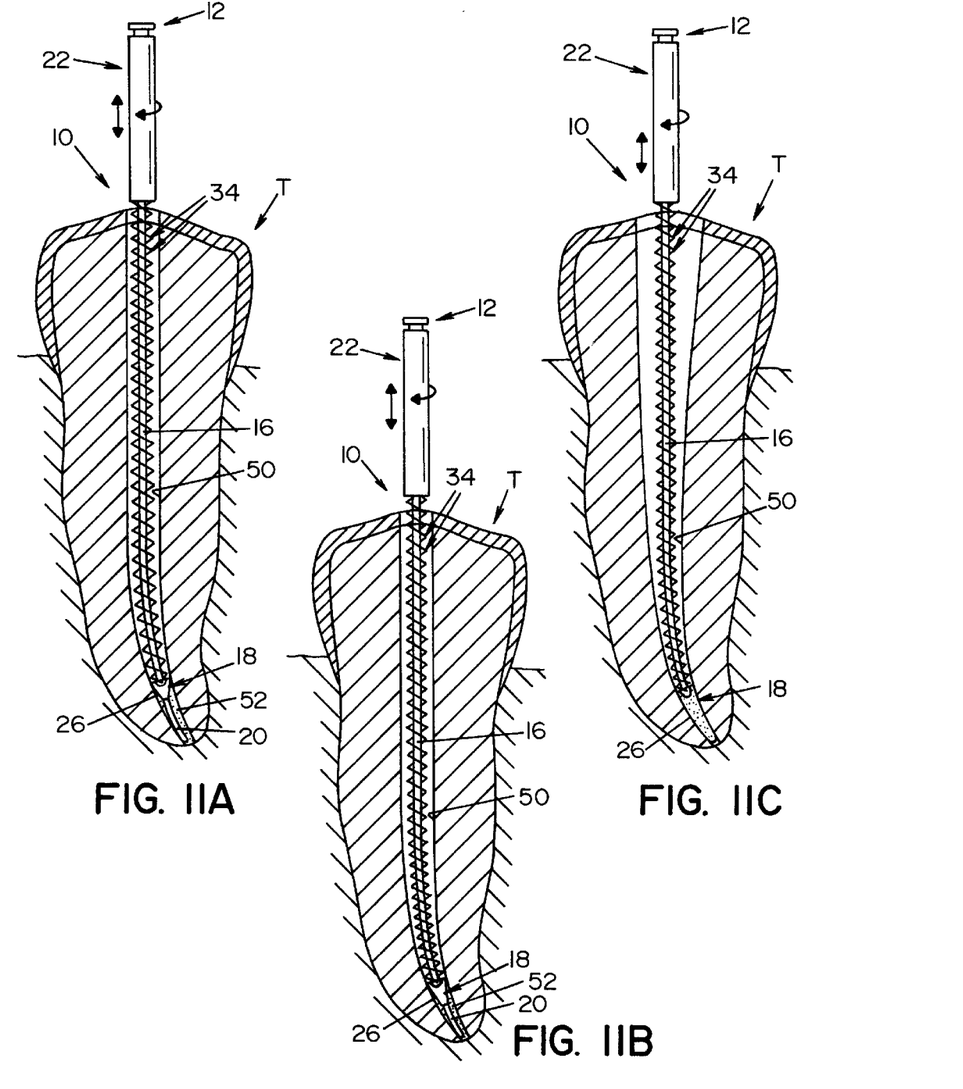

FIGS. 11A, 11B and 11C somewhat schematically illustrate three stages of a root canal therapy procedure using three endodontic instruments of the structure herein illustrated and described and which could be, for example, the instruments depicted in FIG. 8 as having cutting surfaces 26a, 26d and 26f, respectively. While three are shown, it will be appreciated that additional instruments could be used between the stages represented by FIGS. 11A, 11B and 11C. In any event, a tooth T to be subjected to the root canal process has a root canal 50 which contains infected tissue 52 to be removed by the root canal therapy. Initially, following the cutting of an opening into the upper end of the root canal, the first endodontic instrument is employed to remove the tissue 52 from an upper end portion of the root canal and to somewhat enlarge the canal so as to assure complete removal of all of the infected tissue along that portion of the canal for which the first instrument is designed to be used. During movement of the instrument into the root canal, follower portion 20 flexes and follows the path of the canal, and the smoothness of the follower and the rounded distal end thereof preclude the follower from laterally gouging or cutting into the root canal wall as often occurs in the use of endodontic instruments heretofore available. When the procedure reaches the stage shown in FIG. 11B, the frusto-conical cutting surface 26 of the instrument continues to remove the infected tissue 52 in the direction toward the apical foramen of the root canal. It is to be noted that both the shaft 16 and follower 20 of the instrument are flexible so as to assure removal of the infected tissue and enlarging of the canal wall without laterally enlarging or gouging the wall on one side of the path of movement of the instrument as the result of stiffness of the instrument. When the procedure reaches the stage depicted in FIG. 11C, all of the infected tissue has been removed and the root canal enlarged sufficiently for receiving a filling, and flexure of shaft 16 provides for cutting surface 26 to clean and enlarge the root canal to the apical foramen end thereof without the lateral enlargement or gouging which distorts the desired contour for the root canal between its opposite ends. Accordingly, it will be appreciated that enlarging of the canal as used herein with respect to the function of the endodontic instruments of the invention is a uniform enlargement for the purpose of preparing the root canal to receive a filling. Advantageously, as set forth hereinabove, should stem 16 breakaway from cutting head 18 during the procedure, retaining members 34 preclude complete separation of the stem and cutting head from one another and can be grasped and pulled axially and laterally outwardly of the root canal to facilitate removal of the cutting head therefrom.

While considerable emphasis has been placed herein on the preferred embodiments of the invention illustrated and described, it will be appreciated that many embodiments of the invention can be made and that many changes can be in the embodiments disclosed without departing from the principles of the invention. Accordingly, it is to be distinctly understood that the descriptive matter herein is to be interrupted merely as illustrative of the invention and not as a limitation.

Having thus described the invention, it is so claimed:

1. A set of endodontic instruments for use in performing root canal therapy on a tooth, each instrument having a proximal end and a distal end, a shaft extending from said proximal end to a location spaced from said proximal end toward said distal end, a cutting head at said location including a frusto-conical cutting surface having a base end and a second end spaced from said base end in the direction toward said distal end, said cutting surface tapering inwardly from said base end toward said second end, and a follower extending from said second end of said cutting surface to said distal end, the cutting surfaces of the instruments of said set having different lengths and different angles of taper between said base end and said second end thereof.

2. A set of instruments according to claim 1, wherein said cutting surface includes diamond dust.

3. A set of instrument according to claim 1, wherein said shaft has an axis and said base end of said cutting surface is defined by a planar surface on said cutting head transverse to said axis, and means providing at least one passage between said planar surface and said cutting surface.

4. A set of instruments according to claim 3, wherein said base end has a circular periphery truncated by at least one axially extending planar surface to provide said at least one passage.

5. A set of instruments according to claim 4, wherein said axially extending planar surface is parallel to said axis.

6. A set of instruments according to claim 3, wherein said base end has a circular periphery truncated by diametrically opposed axially extending planar surfaces parallel to said axis.

7. A set of instruments according to claim 1, wherein said base end of said cutting surface has a peripheral edge and said cutting head further includes a reinforcing portion extending from said base end toward said proximal end and having a peripheral edge at said base end corresponding in contour to said peripheral edge of said base end.

8. A set of instruments according to claim 7, wherein said reinforcing portion is integral with said cutting surface at said base end thereof.

9. A set of instruments according to claim 8, wherein said reinforcing portion has a terminal end spaced from said base end toward said proximal end and a peripheral outer surface between said base end and said terminal end.

10. A set of instruments according to claim 9, and means providing at least one passage between said terminal end of said reinforcing portion and said cutting surface.

11. A set of instruments according to claim 10, wherein said cutting surface includes diamond dust.

12. A set of instruments according to claim 10, wherein said shaft has an axis, and said base end and said peripheral surface are circular and truncated by diametrically opposed planar surfaces parallel to said axis.

13. A set of instruments according to claim 7, wherein said shaft has an axis and said base end of said cutting surface is defined by a planar surface transverse to said axis, said reinforcing portion being attached to said planar surface.

14. A set of instruments according to claim 13, wherein said shaft is connected to said planar surface and said reinforcing portion surrounds said shaft and includes an outer surface converging toward said shaft in the direction from said planar surface toward said proximal end.

15. A set of endodontic instruments for use in performing root canal therapy on a tooth, each instrument having a proximal end and a distal end, a shaft extending from said proximal end to a location spaced from said proximal end toward said distal end, a cutting head at said location including a frusto'conical cutting surface having a base end and a second end spaced from said base end in the direction toward said distal end, said cutting surface tapering inwardly from said base end toward said second end, and a follower extending from said second end of said cutting surface to said distal end, the cutting surfaces of the instruments of said set having different lengths and different angles of taper between said base end and said second end thereof, and each said instrument further including at least one retaining member having opposite ends connected one to the cutting head and the other to the shaft at a location therealong spaced from said head toward said proximal end.

16. A set of instruments according to claim 15, wherein said cutting surface includes diamond dust.

17. A set of instruments according to claim 15, wherein said retaining member is wire.

18. A set of instruments according to claim 17, wherein said wire is helically wound about said shaft.

19. A set of endodontic instruments for use in performing root canal therapy on a tooth, each instrument having a proximal end and a distal end, a shaft extending from said proximal end to a location spaced from said proximal end toward said distal end, a cutting head at said location including a frusto-conical cutting surface having a base end and a second end spaced from said base end in the direction toward said distal end, said cutting surface tapering inwardly from said base end toward said second end, and a follower extending from said second end of said cutting surface to said distal end, the cutting surfaces of the instruments of said set having different lengths and different angles of taper between said base end and said second end thereof, each instrument further includes at least one retaining member having opposite ends connected one to the cutting head and the other to the shaft at a location therealong spaced from said head toward said proximal end, said retaining member is wire, said wire is helically wound about said shaft, said wire being a first wire and a second wire helically wound about said shaft, said first and second wires being wound about said shaft in opposite directions.

20. A set of instruments according to claim 19, wherein each said first and second wire is spaced outwardly of said shaft.

21. A set of endodontic instruments for use in performing root canal therapy on a tooth, each instrument having a proximal end and a distal end, a shaft extending from said proximal end to a location spaced from said proximal end toward said distal end, a cutting head at said location including a frusto-conical cutting surface having a base end and a second end spaced from said base end in the direction toward said distal end, said cutting surface tapering inwardly from said base end toward said second end, and a follower extending from said second end of said cutting surface to said distal end, the cutting surfaces of the instruments of said set having different lengths and different angles of taper between said base end and said second end thereof, each instrument further including at least two retaining springs helically wound about said shaft in opposite directions and each having a first end attached to said cutting head and a second end attached to said shaft at a location spaced from said head toward said proximal end.

22. A set of instruments according to claim 21, wherein each of said retaining springs is spaced outwardly of said shaft.

23. A set of instruments according to claim 22, wherein said cutting surface includes diamond dust.

24. A set of endodontic instruments for use in performing root canal therapy on a tooth, each instrument having a proximal end and a distal end, a shaft extending from said proximal end to a location spaced from said proximal end toward said distal end, a cutting head at said location including a frusto-conical cutting surface having a base end and a second end spaced from said base end in the direction toward said distal end, said cutting surface tapering inwardly from said base end toward said second end, a follower extending from said second end of said cutting surface to said distal end, the cutting surfaces of the instruments of said set having different lengths and different angles of taper between said base end and said second end thereof, said shaft having an axis and said base end of said cutting surface being defined by a planar surface on said cutting head transverse to said axis, means providing at least one passage between said planar surface and said cutting surface, and each instrument further including at least one retaining member having opposite ends connected one to the cutting head and the other to the shaft at a location therealong spaced from said head toward said proximal end.

25. A set of endodontic instruments for use in performing root canal therapy on a tooth, each instrument having a proximal end and a distal end, a shaft extending from said proximal end to a location spaced from said proximal end toward said distal end, a cutting head at said location including a frusto-conical cutting surface having a base end and a second end spaced from said base end in the direction toward said distal end, said cutting surface tapering inwardly from said base end toward said second end, and a follower extending from said second end of said cutting surface to said distal end, the cutting surfaces of the instruments of said set having different lengths and different angles of taper between said base end and said second end thereof, said shaft has an axis and said base end of said cutting surface is defined by a planar surface on said cutting head transverse to said axis, and means providing at least one passage between said planar surface and said cutting surface, each instrument further includes at least one retaining member having opposite ends connected one to the cutting head and the other to the shaft at a location therealong spaced from said head toward said proximal end, said base end having a circular periphery truncated by at least one axially extending planar surface to provide said at least one passage.

26. A set of instruments according to claim 25, wherein said one end of said retaining member is connected to said axially extending planar surface.

27. A set of endodontic instruments for use in performing root canal therapy on a tooth, each instrument having a proximal end and a distal end, a shaft extending from said proximal end to a location spaced from said proximal end toward said distal end, a cutting head at said location including a frusto-conical cutting surface having a base end and a second end spaced from said base end in the direction toward said distal end, said cutting surface tapering inwardly from said base end toward said second end, and a follower extending from said second end of said cutting surface to said distal end, the cutting surfaces of the instruments of said set having different lengths and different angles of taper between said base end and said second end thereof, said shaft has an axis and said base end of said cutting surface is defined by a planar surface on said cutting head transverse to said axis, and means providing at least one passage between said planar surface and said cutting surface, each instrument further including at least two retaining springs helically wound about said shaft in opposite directions and each having a first end attached to said cutting head and a second end attached to said shaft at a location spaced from said head toward said proximal end.

28. A set of instruments according to claim 27, wherein said base end has a circular periphery truncated by diametrically opposed axially extending planar surface parallel to said axis.

29. A set of instruments according to claim 28, wherein the first end of each of said retaining springs is attached to a different one of said diametrically opposed planar surfaces.

30. A set of endodontic instruments for use in performing root canal therapy on a tooth, each instrument having a proximal end and a distal end, a shaft extending from said proximal end to a location spaced from said proximal end toward said distal end, a cutting head at said location including a frusto-conical cutting surface having a base end and a second end spaced from said base end in the direction toward said distal end, said cutting surface tapering inwardly from said base end toward said second end, a follower extending from said second end of said cutting surface to said distal end, the cutting surfaces of the instruments of said set having different lengths and different angles of taper between said base end and said second end thereof, said base end of said cutting surface having a peripheral edge, said cutting head further including a reinforcing portion extending from said base end toward said proximal end and having a peripheral edge at said base end corresponding in contour to said peripheral edge of said base end, said reinforcing portion being integral with said cutting surface at said base end thereof, and having a terminal end spaced from said base end toward said proximal end and a peripheral outer surface between said base end and said terminal end, means providing at least one passage between said terminal end of said reinforcing portion and said cutting surface, and each instrument further including at least one retaining member having opposite ends connected one to the cutting head and the other to the shaft at a location therealong spaced from said head toward said proximal end.

31. A set of endodontic instruments for use in performing root canal therapy on a tooth, each instrument having a proximal end and a distal end, a shaft extending from said proximal end to a location spaced from said proximal end toward said distal end, a cutting head at said location including a frusto-conical cutting surface having a base end and a second end spaced from said base end in the direction toward said distal end, said cutting surface tapering inwardly from said base end toward said second end, and a follower extending from said second end of said cutting surface to said distal end, the cutting surfaces of the instruments of said set having different lengths and different angles of taper between said base end and said second end thereof, said base end of said cutting surface has a peripheral edge and said cutting head further includes a reinforcing portion extending from said base end toward said proximal end and having a peripheral edge at said base end corresponding in contour to said peripheral edge of said base end, said reinforcing portion is integral with said cutting surface at said base end thereof, said reinforcing portion has a terminal end spaced from said base end toward said proximal end and a peripheral outer surface between said base end and said terminal end, means providing at least one passage between said terminal end of said reinforcing portion and said cutting surface, each instrument further including at least two retaining springs helically wound about said shaft in opposite directions and each having a first end attached to said cutting head and a second end attached to said shaft at a location spaced from said head toward said proximal end.

32. A set of instruments according to claim 31, wherein said shaft has an axis, said base end and said peripheral surface are circular and truncated by diametrically opposed planar surfaces parallel to said axis.

33. A set of instruments according to claim 32, wherein said first ends of said springs are each attached to a different one of said diametrically opposed planar surfaces.

34. A set of instruments according to claim 33, wherein said cutting surface includes diamond dust.

35. A set of endodontic instruments for use in performing root canal therapy on a tooth, each instrument having a proximal end and a distal end, a shaft extending from said proximal end to a location spaced from said proximal end toward said distal end, a cutting head at said location including a frusto-conical cutting surface having a base end and a second end spaced from said base end in the direction toward said distal end, said cutting surface tapering inwardly from said base end toward said second end, and a follower extending from said second end of said cutting surface to said distal end, the cutting surfaces of the instruments of said set having different lengths and different angles of taper between said base end and said second end thereof, said base end of said cutting surface has a peripheral edge and said cutting head further includes a reinforcing portion extending from said base end toward said proximal end and having a peripheral edge at said base end corresponding in contour to said peripheral edge of said base end, said shaft has an axis and said base end of said cutting surface is defined by a planar surface transverse to said axis, said reinforcing portion being attached to said planar surface, said shaft is connected to said planar surface and said reinforcing portion surrounds said shaft and includes an outer surface converging toward said shaft in the direction from said planar surface toward said proximal end, each instrument further including at least two retaining springs helically wound about said shaft in opposite directions and each having a first end attached to said cutting head and a second end attached to said shaft at a location spaced from said head toward said proximal end.

36. A set of instruments according to claim 35, wherein the first end of each retaining spring is embedded in said reinforcing portion.

37. A set of instruments according to claim 36, wherein each of said retaining springs is spaced outwardly of said shaft.

38. A set of instruments according to claim 37, wherein said cutting surface includes diamond dust.

39. An endodontic instrument for use in performing root canal therapy on a tooth, said instrument having a proximal end and a distal end, a shaft extending from said proximal end toward said distal end, a cutting head on said shaft between said proximal and distal ends, and at least one retaining member having opposite ends connected one to the cutting head and the other to the shaft at a location therealong spaced from said head toward said proximal end.

40. An instrument according to claim 39, wherein said retaining member is wire.

41. An instrument according to claim 40, wherein said wire is spring wire.

42. An instrument according to claim 40, wherein said wire is helically wound about said shaft.

43. An endodontic instrument for use in performing root canal therapy on a tooth, said instrument having a proximal end and a distal end, a shaft extending from said proximal end toward said distal end, a cutting head on said shaft between said proximal and distal ends, and at least one retaining member having opposite ends connected one to the cutting head and the other to the shaft at a location therealong spaced from said head toward said proximal end, said retaining member is wire, said wire being a first wire, and a second wire providing a second retaining member.

44. An endodontic instrument for use in performing root canal therapy on a tooth, said instrument having a proximal end and a distal end, a shaft extending from said proximal end toward said distal end, a cutting head on said shaft between said proximal and distal ends, and at least one retaining member having opposite ends connected one to the cutting head and the other to the shaft at a location therealong spaced from said head toward said proximal end, said retaining member is wire, said wire is helically wound about said shaft, said wire being a first wire and a second wire helically wound about said shaft, said first and second wires being wound about said shaft in opposite directions.

45. An instrument according to claim 44, wherein each said first and second wire is spaced outwardly of said shaft.

46. An instrument according to claim 44, wherein said first and said second wires are each spring wire.

47. An instrument according to claim 46, wherein each said first and second wire is spaced outwardly of said shaft.

48. An endodontic instrument for use in performing root canal therapy on a tooth, said instrument having a proximal end and a distal end, a shaft extending from said proximal end toward said distal end, a cutting head on said shaft between said proximal and distal ends, and at least one retaining member having opposite ends connected one to the cutting head and the other to the shaft at a location therealong spaced from said head toward said proximal end, said retaining member is wire, said wire being a first wire, and a second wire providing a second retaining member, each said first and second wire being spring wire.

49. An endodontic instrument for use in performing root canal therapy on a tooth, said instrument having a proximal end and a distal end, a shaft extending from said proximal end toward said distal end, a cutting head on said shaft between said proximal and distal ends, and at least one retaining member having opposite ends connected one to the cutting head and the other to the shaft at a location therealong spaced from said head toward said proximal end, said at least one retaining member including two retaining springs helically wound about said shaft in opposite directions and each having a first end attached to said cutting head and a second end attached to said shaft.

* * * * *